United States Patent [19]
Young et al.

[11] Patent Number: 6,117,091
[45] Date of Patent: Sep. 12, 2000

[54] ANORECTAL ANGLE MEASUREMENT

[75] Inventors: Howard Lewis Young, Cardiff; Richard Herbert Lowndes, Norwich, both of United Kingdom

[73] Assignee: University of Wales College of Medicine, Cardiff, United Kingdom

[21] Appl. No.: 09/043,466
[22] PCT Filed: Sep. 20, 1996
[86] PCT No.: PCT/GB96/02296
  § 371 Date: May 13, 1998
  § 102(e) Date: May 13, 1998
[87] PCT Pub. No.: WO97/10746
  PCT Pub. Date: Mar. 27, 1997

[30] Foreign Application Priority Data

Sep. 20, 1995 [GB] United Kingdom .................... 9519194

[51] Int. Cl.[7] .................................................. A61B 5/103
[52] U.S. Cl. ............................................ 600/587; 600/593
[58] Field of Search .................................... 600/587, 588, 600/591, 593, 595

[56] References Cited

U.S. PATENT DOCUMENTS 4,366,810   1/1983   Slanetz, Jr. .
4,687,002   8/1987   Lahr .
4,873,990   10/1989  Holmes et al. .

Primary Examiner—Max Hindenburg
Assistant Examiner—Pamela L Wingood
Attorney, Agent, or Firm—Young & Thompson

[57] ABSTRACT

Apparatus (10) for measuring the anorectal angle comprises an outer rubber-like sheath (12), which may be a suitably modified catheter, within which is disposed an elongate angular deflection detector (14) which provides on display (16) a read-out of the angular deflection of the apparatus. The sheath (12) may include pressure ports with associated pressure lines back to the proximal end of the sheath to allow the pressure to be read at different points along the anal canal.

14 Claims, 1 Drawing Sheet

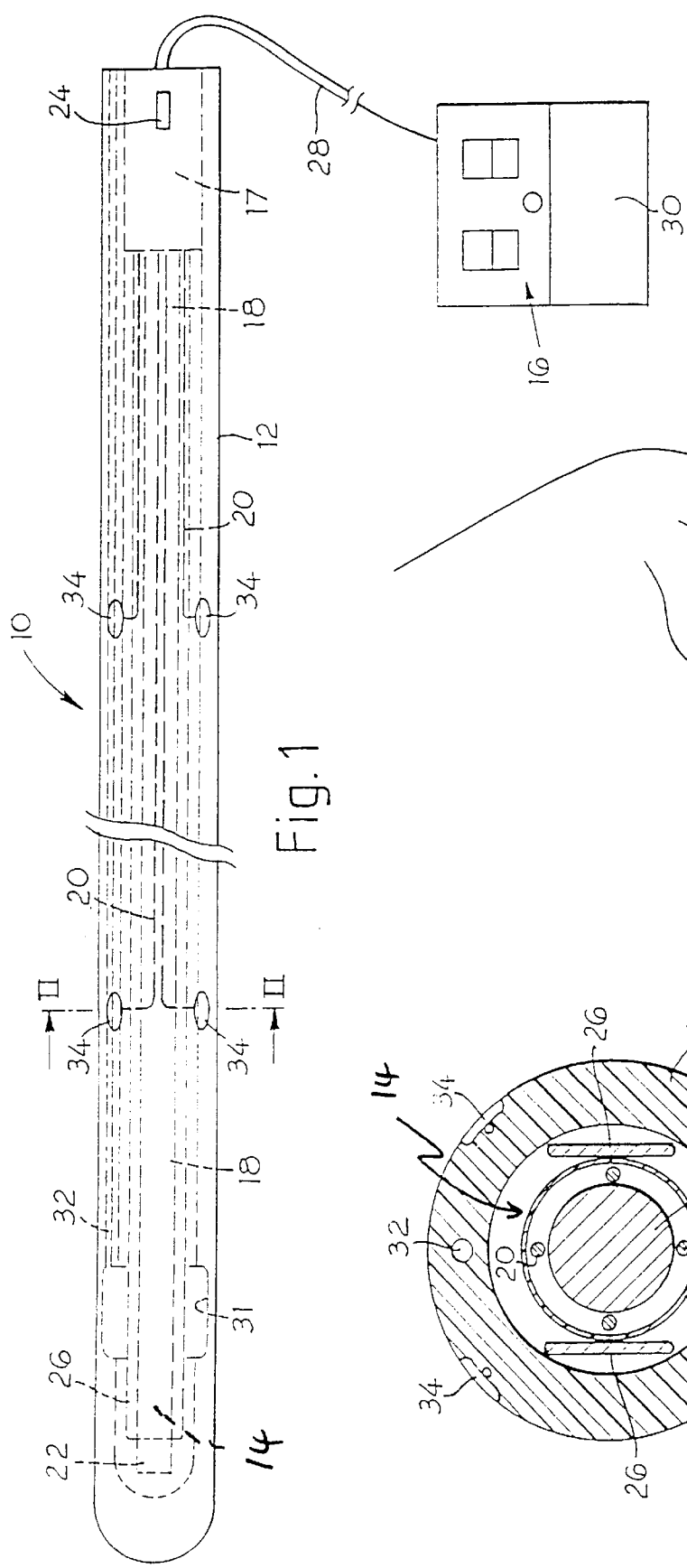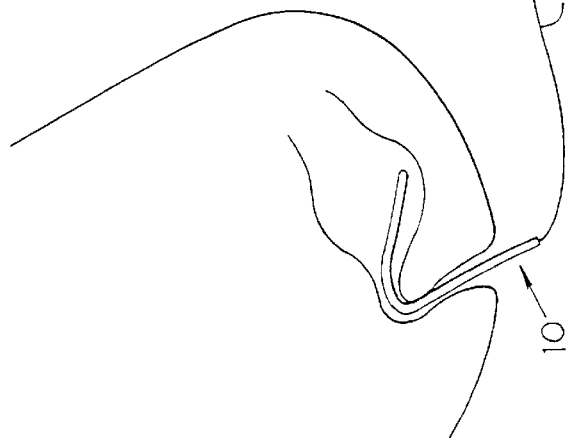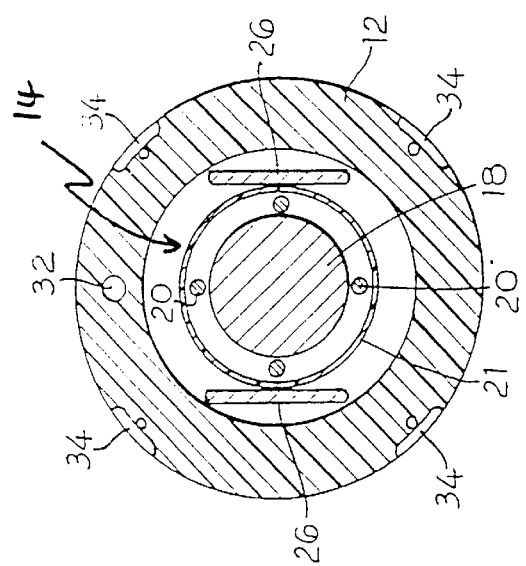

ANORECTAL ANGLE MEASUREMENT

This invention relates to apparatus and methods for measuring the anorectal angle and more generally to apparatus and methods for measuring, monitoring or observing the local anatomy or selected parameters in the anal canal and/or rectum.

Measurement of the anorectal angle (the angle of the anus relative to the rectum) is part of the investigations undertaken to determine the functionality of the anal canal and rectum in patients suffering defecatory disorders. The passage of stools is controlled by a muscular sling which controls the anorectal angle, between an acute angle (closed) and an obtuse angle (open). Lack of proper control can lead to constipation or faecal incontinence. In addition to anorectal angle, the manometric pressure at various points in the rectum and anal canal may be detected, and electromyological readings may be taken to determine muscle activity.

Generally, the measurement of the anorectal angle has been performed by inserting into the rectum of the patient a radiological contrast medium which has the consistency of a soft stool, to simulate a soft faecal motion. The patient then sits on a radiolucent toilet and is screened radiologically whilst defecating. The difference between the angle of the rectum before and during defecation provides some indication as to whether there may be a functional disorder of the anorectum in patients who have problems in defecating. This procedure is referred to as a defecating proctogram and is unpleasant for the patient, invasive (requiring exposure to radiation) and many Radiological Units will not or cannot perform the procedure. The procedure also of course requires special equipment and a skilled radiologist to observe and interpret the results.

A need therefore exists for an apparatus and method for use in monitoring the anal canal and/or rectum, for example for measuring anorectal angle which, alleviates at least some of the above problems, allowing the measurement to be carried out more widely.

Accordingly, in one aspect, this invention provides a method for use in monitoring the anal canal and/or rectum of a patient, which comprises inserting through the anus into the rectum an elongate flexible element and measuring or observing the angular deflection of said flexible element, and/or the contour adopted thereby.

Preferably, said angular deflection is measured in a single plane, for example the horizontal plane if the patient is lying on his or her side.

Preferably the change of said angular deflection is measured during a simulated defecatory process.

Preferably, said angular deflection is measured using a sensor associated with said elongate flexible element.

Thus in preferred embodiments of this invention, the anorectal angle may be measured without requiring exposure to radiation and without requiring the patient to defecate.

In another aspect, this invention provides apparatus for use in monitoring the anal canal and/or rectum of a patient, which apparatus comprises an elongate flexible element designed to be introduced via the anus into the rectum and having associated therewith angular deflection detecting means for detecting the angular deflection thereof and/or the contour adopted by said flexible element.

Preferably, said angular deflection detecting means comprises an elongate flexible core element and sensor means responsive to longitudinal strain disposed along opposed sides of the core element to determine angular deflection between spaced regions thereof. In one embodiment, the sensor means comprise respective elongate strain gauges extending along substantially the whole length of the elongate flexible core element at circumferentially spaced locations.

Preferably said elongate flexible element comprises a rubber or rubber-like outer sheath within which is disposed said angular deflection detecting means.

Preferably, said outer sheath includes an inflatable region in the distal position thereof, and whereby said region may be inflated in use to stimulate the rectum.

Preferably, said apparatus includes pressure detecting means for determining in use the pressure acting in the rectum or adjacent the anus. The pressure detecting means may comprise one or more pressure sensors located in the outer sheath or pressure ports disposed in the outer sheath leading to one or more associated sensors.

In this way, a single instrument may be provided which provides a reading of anorectal angle and manometric pressure, and so a 3-D pressure map of pressures within the anorectal region may be constructed.

In a further aspect, this invention provides use of the apparatus as defined as a bio-feedback sensor for training patients with defecatory disorders.

Whilst the invention has been described above, it extends to any inventive combination of features set out above or in the following description.

The invention may be performed in a various ways and an embodiment thereof will now be described in detail, reference being made to the accompanying drawings in which:

FIG. 1 is a schematic side view of apparatus in accordance with this invention;

FIG. 2 is a cross sectional view on an enlarged scale of the apparatus of FIG. 1, and FIG. 3 is a schematic view showing the apparatus in use.

The apparatus 10 for measuring anorectal angle comprises an outer rubber-like sheath 12, which may be a suitably modified catheter, within which is disposed an elongate angular deflection detector 14 which provides on display 16 a read-out of the angular deflection of the apparatus.

Referring to FIGS. 1 and 2, the angular deflection detector 14 comprises an anchorage or "fixed" end 17 from which extends a core element 18 of flexible wire or cable and four strain gauge wires 20 extending along the length of the core and equispaced at 90° around the core, the whole being covered in thin plastics cover 21 (see FIG. 2). Such a detector is obtainable from Penny and Giles Limited, Blackwood, Gwent, U.K.

The strains experienced by the strain gauge wires 20 are calculated to determine the total strain acting along the whole core on all four sides, thereby to determine the angular deflection between the tip 22 and the anchorage 17. In this particular example, only deflections in the plane of the section shown in FIG. 3 are monitored. The apparatus includes a mark 24 on the outer sheath to ensure that the instrument is used in the correct orientation. Also, as the accuracy of this particular sensor will be degraded if the angular deflection detector 14 is twisted, the apparatus includes thin flexible strips 26 to either side of the detector to ensure that flexing of the apparatus is confined to the single plane only. From the anchorage 17 the signals are fed by a cable 28 to a processor 30 which drives the display 16. The output is also available to interface with a suitable PC/software package (not shown) to allow the output from the instrument to sampled, correlated and/or combined with data from the other sensors for further processing as required.

The outer sheath 12 has a central bore in which the deflection detector 14 and strips 26 are snugly located, and the sheath 12 is bonded to the detector anchorage 17. The sheath induces an inflatable balloon chamber 31 at its distal end, fed by a line 32 which runs back to the proximal end of the device. Likewise eight pressure sample points 34 are located along the extension of the sheath and respective passages run back to the distal end.

In use, the apparatus is inserted into the anus of a patient with the mark 24 aligned with the anterior plane of the patient and pushed in until the distal end is well into the patient's rectum, as seen in FIG. 3. Measurements of angle and pressure may been be taken. The balloon 31 may be inflated to stimulate defecation or the patient may be asked to push, and the corresponding change in angle measured.

The apparatus gives a quick read out which does not require interpretation to determine the actual angle, and so a numerical score can be given easily. There is minimal invasion of patient privacy compared to the defecating proctogram.

The apparatus is especially suited to bio-feedback, as a patient may be given the apparatus and instructed to practice regularly to obtain a particular angle on the display. In this way, the patient may relearn the appropriate response which may have been lost previously.

We claim:

1. A method for monitoring at least one of the anal canal and rectum of a patient, which method comprises inserting via the anus into the rectum an elongate flexible element, said elongate flexible element having incorporated therein angular deflection sensor means for detecting the angular deflection of said elongate flexible element, and monitoring the output of said angular deflection sensor means.

2. A method according to claim 1, wherein said angular deflection is measured in a single plane.

3. A method according to claim 1, wherein the change of said angular deflection is measured during a simulated defecatory process.

4. A method according to claim 1 wherein said angular deflection sensor means comprises a plurality of strain sensors associated with said elongate flexible element.

5. A method according to claim 1, which further includes monitoring the pressure at one or more points in at least one of the anal canal and the rectum using at least one pressure sensor means provided on said elongate flexible element.

6. Apparatus for use in monitoring the anal canal or rectum of a patient, which apparatus comprises an elongate flexible element designed to be introduced via the anus into the rectum, said elongate flexible element having incorporated therein angular deflection sensor means for detecting angular deflection of said element.

7. Apparatus according to claim 6, wherein said angular deflection sensor means comprises an elongate flexible core element and a sensor arrangement responsive to longitudinal strain along opposed sides of the core element to determine angular deflection between spaced regions thereof.

8. Apparatus according to claim 7, wherein the sensor arrangement comprises respective elongate strain gauges extending along substantially the whole length of the elongate flexible core element at radially spaced locations.

9. Apparatus according to claim 6, wherein said elongate flexible element comprises a rubber or rubber-like outer sheath surrounding said angular deflection sensor means.

10. Apparatus according to claim 9, wherein said outer sheath includes an inflatable region in the distal position thereof, whereby said region may be inflated in use to stimulate the rectum.

11. Apparatus according to any of claim 6, wherein said apparatus includes pressure detecting means for determining in use the pressure acting in the rectum or adjacent the anus.

12. Apparatus according to claim 11, wherein the pressure detecting means comprises one or more pressure sensors located in the outer sheath or pressure ports disposed in the outer sheath leading to one or more associated sensors.

13. A bio-feedback sensor for training a patient with a defecatory disorder, comprising an elongate flexible element designed to be introduced via the anus into the rectum and having incorporated in said flexible element angular deflection sensor means for detecting angular deflection of said element, and means for indicating to the user the deflection of said element.

14. A method according to claim 1, which includes using said angular deflection sensor means to detect the contour adopted by said elongate flexible element.

* * * * *